US005783663A

United States Patent [19]

Mondorf et al.

[11] Patent Number: 5,783,663
[45] Date of Patent: Jul. 21, 1998

[54] PEPTIDE LIGANDS FOR AFFINITY PURIFICATION OF FIBRINOGEN

[75] Inventors: Kristine Mondorf; Ruben C. Carbonell; Joseph A. Buettner, all of Raleigh, N.C.

[73] Assignee: Bayer Corporation, Berkeley, Calif.

[21] Appl. No.: 12,343

[22] Filed: Jan. 23, 1998

[51] Int. Cl.$^6$ .............................. A61K 38/08; C07K 7/06
[52] U.S. Cl. ................................ 530/329; 530/382
[58] Field of Search ............................ 530/329, 382

[56] References Cited

PUBLICATIONS

Baumbach et al. Protein purification using affinity ligands from peptide libraries. BioPharm. 24–35, May 1992.
Buettner et al. Chemically derived peptide libraries: A new resin and methodology for lead identification. Int. J. Peptide Protein Res. 47:70–83, 1996.
Smith et al. A ribonuclease S–peptide antagonist discovered with a bacteriophage display library. Gene 128:37–42, 1993.
Brennan, M. Fibrin glue. Blood Reviews 5:240–244, 1991.

*Primary Examiner*—Cecilia J. Tsang
*Assistant Examiner*—Cecilia F. Wang
*Attorney, Agent, or Firm*—Michael J. Beck; James A. Giblin

[57] ABSTRACT

Peptides which bind to fibrinogen are disclosed. These peptides have available fibrinogen binding domains having a Trp-Gln-Glu-His-Tyr-Asn, Trp-Gln-Glu-Thr-TyrGln,or Tyr-Glu-Asn-Tyr-Gly-Tyr sequence. Peptides containing at least one of these fibrinogen binding domains are immobilized upon a chromatographic substrate in a preferred embodiment of the invention. This preferred embodiment is useful in an affinity chromatography process to purify fibrinogen.

2 Claims, 3 Drawing Sheets

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
 ( A ) LENGTH: 6
 ( B ) TYPE: amino acid
 ( C ) STRANDEDNESS: single strand
 ( D ) TOPOLOGY: linear ( i i ) MOLECULE TYPE:
 ( A ) DESCRIPTION: peptide ( x i ) SEQUENCE DESCRIPTION: SEQ ID NO:1:

Trp Gln Glu His Tyr Asn
1               5

( 2 ) INFORMATION FOR SEQ ID NO:2:

( i ) SEQUENCE CHARACTERISTICS:
 ( A ) LENGTH: 6
 ( B ) TYPE: amino acid
 ( C ) STRANDEDNESS: single strand
 ( D ) TOPOLOGY: linear ( i i ) MOLECULE TYPE:
 ( A ) DESCRIPTION: peptide ( x i ) SEQUENCE DESCRIPTION: SEQ ID NO:2:

Trp Gln Glu Thr Tyr Gln
1               5

( 2 ) INFORMATION FOR SEQ ID NO:3:

( i ) SEQUENCE CHARACTERISTICS:
 ( A ) LENGTH: 6
 ( B ) TYPE: amino acid
 ( C ) STRANDEDNESS: single strand
 ( D ) TOPOLOGY: linear ( i i ) MOLECULE TYPE:
 ( A ) DESCRIPTION: peptide ( x i ) SEQUENCE DESCRIPTION: SEQ ID NO:3:

Tyr Glu Asn Tyr Gly Tyr
1               5

( 2 ) INFORMATION FOR SEQ ID NO:4:

( i ) SEQUENCE CHARACTERISTICS:
 ( A ) LENGTH: 6
 ( B ) TYPE: amino acid
 ( C ) STRANDEDNESS: single strand
 ( D ) TOPOLOGY: linear ( i i ) MOLECULE TYPE:
 ( A ) DESCRIPTION: peptide ( x ) PUBLICATION INFORMATION:
 ( A ) AUTHORS: Smith, G. P.
   Schultz, D. A.
   Ladbury, J. E.
 ( B ) TITLE: A Ribonuclease S-Peptide Antagonist Discovered
   with a Bacteriophage Display Library
 ( C ) JOURNAL: Gene
 ( D ) VOLUME: 128
 ( F ) PAGES: 37-42

( x i ) SEQUENCE DESCRIPTION: SEQ ID NO:4:

Tyr Asn Phe Glu Val Leu
1               5

( 2 ) INFORMATION FOR SEQ ID NO:5:

( i ) SEQUENCE CHARACTERISTICS:

( A ) LENGTH: 6
            ( B ) TYPE: amino acid
            ( C ) STRANDEDNESS: single strand
            ( D ) TOPOLOGY: linear ( i i ) MOLECULE TYPE:
            ( A ) DESCRIPTION: peptide ( x i ) SEQUENCE DESCRIPTION: SEQ ID NO:5:

Trp Glu Gln Ser Asn Pro
 1               5

PEPTIDE LIGANDS FOR AFFINITY PURIFICATION OF FIBRINOGEN

BACKGROUND OF THE INVENTION

1. Field

This invention is concerned generally with identifying protein-ligand interactions, and specifically with peptide ligands which bind fibrinogen and which may be used in a method for the affinity purification of fibrinogen.

2. Background

Affinity chromatography is one of the most efficient techniques for purifying a protein from a complex mixture. With potential advantages including high stability, efficiency, selectivity, and low price, peptides have been investigated as affinity ligands in the pharmaceutical industry. A recent approach for identifying such ligands is to screen peptides from combinatorial peptide libraries (1–4).

Using the "divide, couple, recombine" approach (5–7), millions of unique peptides of a defined length may be synthesized on resin beads. Each bead contains a different peptide sequence. In solid phase screening, this "one-bead-one-structure peptide library" is exposed to a target protein. Those beads and the corresponding peptides to which protein binds must be detected, isolated, and identified. Several detection systems, including colorimetric two-step methods (2, 7, 8) as well as direct fluorescence detection methods (9–11), have been used Colorimetric methods are usually based on a primary and secondary antibody-conjugate system. Antibodies have the potential for being very specific and sensitive. However, antibody-based methods also have the potential for non-specific interactions due to antibody and antibody-conjugate adsorption to the peptide library itself. These two-step methods also consist of more variables than one-step methods, thus requiring additional optimization. With direct fluorescent detection methods, autofluorescence of the resin beads can be a major draw-back, depending on the type of resin used (12).

In 1993, Kassarjian et al. introduced a radiological approach to screening peptide libraries against an $^{125}$I-labeled target (13, 14). A similar methodology was also used for the determination of substrate motifs for protein kinases using $^{32}$P-ATP (15, 16). First, peptide library beads were incubated with radiolabeled target, washed, and immobilized as a monolayer in agarose gel. The gel was then dried and exposed to autoradiography film. Careful alignment of the film with the gel allowed isolation and identification of peptide beads that bound target protein.

Disadvantages of this technique include the handling of radioactive material and the potential structural modification of target protein due to radiolabeling. Exposure times might also be a limiting factor. Nevertheless, the radiological approach offers direct detection with few parameters, and thereby facilitates optimization of blocking and binding conditions.

Here, the radiological approach is extended to the use of $^{14}$C-labeled proteins. The $^{14}$C isotope offers a longer half-life and is of a less hazardous nature than isotopes like $^{125}$I. Furthermore, any molecules already incorporated with $^{14}$C are suitable targets using this approach. This is particularly advantageous for small molecules, where antibody-related detection is impracticable and modification of the small molecule is undesirable. The objective, therefore, was to detect $^{14}$C-labeled protein bound to a single library bead using autoradiography. This paper shows that this $^{14}$C approach is not only possible, but also sensitive, allowing detection of low levels of radioactivity.

Ribonuclease S-protein, which binds to the peptide YNFEVL (SEQ ID NO 4), serves as a model system (3, 17). Experiments were done to show proof of principle by screening a hexameric library spiked with YNFEVL-beads against $^{14}$C-labeled ribonuclease S-protein; the number of positive signals on autoradiography film were close to the number of YNFEVL-beads spiked into the library.

Finally, the $^{14}$C-radiological approach was applied to identify peptide ligands that bind fibrinogen. This protein is of interest to the pharmaceutical industry, primarily as a component in the topical adhesive "fibrin glue" (18). Several peptides able to capture fibrinogen from a mixture of fibrinogen and albumin are identified, demonstrating that affinity ligands for protein purification may be obtained with this screening approach. Peptides disclosed in the U.S. Pat. application Ser. No. 08/595,718, incorporated herein by reference, also were found to bind fibrinogen (27).

SUMMARY OF THE INVENTION

Peptides characterized by their ability to bind fibrinogen have now been discovered. These peptides have available fibrinogen binding domains having a Trp-Gln-Glu-His-Tyr-Asn, Trp-Gln-Glu-Thr-Tyr-Gln, or Tyr-Glu-Asn-Tyr-Gly-Tyr sequence (SEQ ID NOS 1, 2, and 3, respectively). As used herein, an available fibrinogen binding domain means a peptide sequence which is sterically available to bind with fibrinogen in the surrounding solution and which adopts a conformation that ligates fibrinogen with moderate to strong avidity under controlled conditions of pH, ionic strength, and solvent composition. The avidity of binding may be increased or decreased by altering the amino acids adjacent to the above listed sequences and/or by terminal deletion of amino acids. The avidity may be modified further by altering the above mentioned conditions of pH, ionic strength, and solvent composition.

The peptides were isolated and identified using a radiological screening process. A method of using the peptides in an affinity chromatography process to purify fibrinogen is also described. The method comprises passing a fibrinogen containing solution over a substrate which has bound thereupon peptides disclosed herein, and then eluting the fibrinogen.

SPECIFIC EMBODIMENTS

Materials and Methods

All reactions and processes were performed at room temperature, unless specified otherwise. Deionized water was purified by a Barnstead nanopure water purification system (Dubuque, Iowa).

Synthesis of Combinatorial Peptide Library

The hexameric peptide library was synthesized onto Toyopearl AF Chelate 650M resin (Tosohaas; Montgomeryville, Pa.). The estimated size and weight of these resin beads vary from 65–130 μm/bead and 0.1–1 μg/bead, respectively. In this work, a value of 0.5 μg/bead is used as an average bead weight. Toyopearl AF Chelate 650M resin was rinsed several times with water, methanol, and dimethylformamide (DMF, Burdick & Jackson, Muskegon, Mich.). A linker, 4,7,10-trioxa-1,13-tridecanediamine (TOTDA; Aldrich, St. Louis, Mo.), was coupled onto the resin carboxylate groups using a 5-fold molar excess (over carboxylate groups) of benzotriazole-1-yl-oxy-tris-pyrrolidino-o-phosphonium hexafluorophosphate (PyBOP, Novabiochem, San Diego, Calif.) and a 10-fold molar excess (over carboxylate groups) of N-methylmorpholine (NMM, Aldrich) in DMF. After reacting for 1 hour, the aminated resin was washed several times with DMF and methanol (Aldrich), then dried in vacuo.

Using the "divide, couple, recombine" approach, the hexameric combinatorial peptide library was synthesized on a Gilson AMS 422 (Middleton, Wis.) multiple peptide synthesizer. Coupling and rinsing proceeded with argon bubbling. All natural L-amino acids, excluding Cys and Met, were coupled by standard Fmoc chemistry. Fmoc amino acids were purchased from NovaBiochem (San Diego, Calif.).

In a procedure similar to that of Buettner (2), 18 grams of aminated resin were equally divided into 36 reaction vessels, two for each amino acid coupling. The resin was rinsed six times with DMF. A five-fold molar excess over amino groups of Fmoc-protected amino acid (2 ml of 0.5M in DMF) was activated in situ with PyBOP (1.5 ml of 0.7M in DMF) and NMM (1 ml of 2M in DMF). Coupling proceeded for 45 minutes.

Next, resin from each vessel was pooled and washed several times with DMF using argon agitation. After redistributing the resin equally into the vessels, the Fmoc protecting group of the most recently coupled amino acid was cleaved with 4 ml of 30% (v/v) piperidine (Sigma) in DMF. This five-minute deprotection step was repeated, and the resin was rinsed 5 times with DMF. The coupling cycle was then repeated until the hexamer library was complete.

The library beads were next recombined, washed 5 times with methanol, and dried overnight in vacuo. Side-chain protecting groups were cleaved for four hours using a mixture of trifluoroacetic acid (TFA, Aldrich)-triisopropylsilane (Aldrich)-water-methanol (94:2:2:2, v/v/v/v). The resin was rinsed four times with methanol, then dried in vacuo.

Peptide densities achieved with the above scheme were typically in the range of 0.2–0.5 mmole/g resin.

Synthesis of Individual Peptides

The peptide YNFEVL (SEQ ID NO 4) and peptides found by screening against fibrinogen were synthesized directly onto TOTDA-modified Toyopearl AF 650 Chelate resin at a reduced substitution density of 0.1–0.2 mmole/g resin. This substitution was achieved by coupling a 1:10 ratio of Fmoc-L-Alanine to tBoc-L-Alanine onto the TOTDA linker. Only the Fmoc protecting group is released by alkali; the tBoc protecting group is acid-labile. Thus using Fmoc chemistry, acylation only occurs at the Fmoc-L-Ala sites.

Specifically, 0.91M tBoc-L-Ala and 0.091M Fmoc-L-Ala were activated for 30 minutes with 0.56M N-hydroxybenzotriazole (HOBt, Novabiochem) and 0.82M NMM in DMF. TOTDA-modified chelate resin was added to the solution and mixed. The molar excess of tBoc-L-Ala, HOBt, and NMM over resin free amine groups was roughly 10, 6, and 9, respectively. After 2 hours of alanine coupling, the resin was washed 10 times each with DMF and methanol. Peptides were then synthesized onto the support, washed, and deprotected with TFA as described above.

Peptide composition was confirmed and the degree of substitution of the resin calculated by quantitative amino acid analysis. Each peptide-resin was subjected to propionic acid/HCl hydrolysis (Pierce, Rockford, Ill.) for 2 hours at 155° C. This was performed at Commonwealth Biotechnologies, Inc., Richmond, Va. using a Hewlett Packard Amino Quant Chemistry system (19).

Sequencing was performed at Protein Technologies Laboratories, Texas A&M University, Tex., by Edman degradation using a Hewlett Packard G1005A (20).

Radioactive Labeling

Following the protocol of Jentoft et al. (21), aminated beads (resin modified with TOTDA-linker) and proteins were labeled using reductive $^{14}C$-methylation. The $^{14}C$-methylated beads are hereafter referred to as $^{14}C$-Test Beads. The $^{14}C$-labeled formaldehyde was obtained from Dupont-NEN (55 Ci/mole, Boston, Mass.). Ribonuclease S-protein was purchased from Sigma (St. Louis, Mo.); human fibrinogen, from Chromogenix AB (Molndal, Sweden). To separate $^{14}C$-labeled protein from non-incorporated $^{14}C$-formaldehyde, an Econopac 10DG Desalting Column (Biorad, Hercules, Calif.) was employed. The $^{14}C$-labeled proteins were stored in the labeling buffer, 0.1M sodium phosphate buffer (Fisher, Pittsburgh, Pa.), pH 7, at −18° C. Pure protein solutions were quantitated using $A_{280}$, with extinction coefficients of 1.5 and 0.73 for fibrinogen and S-protein, respectively. The resulting protein concentrations were 30 μM for $^{14}C$-S-protein, and 4 μM for $^{14}C$-fibrinogen. Maximal labeling yield was calculated based on maximum of two $^{14}C$-labeled methyl groups per mole of amino groups.

The number of disintegrations per minute, DPM, of radioactive samples was determined using a 1500 TriCarb Liquid Scintillation Analyzer from Packard (Meridan, Conn.) and CytoScint ES scintillation liquid from ICN (Casta Mesa, Calif.). Values of DPM are corrected for the background of the liquid scintillation counter (30–35 DPM) unless specified otherwise.

Sensitivity Tests of $^{14}$C-Autoradiography

To obtain a wide range in the values of DPM per bead, $^{14}$C-labeled formaldehyde was reacted with TOTDA-chelate beads at ratios of 0.1, 0.2, 0.4, 1.0, and 2 μmol H$^{14}$CHO per 2 mg of TOTDA-beads. Following the labeling reaction, the beads were washed until the rinse reached background DPM levels. Single beads, 10 from each ratio, were counted in the scintillation counter for 20 minutes to estimate the DPM range. This yielded a standard deviation of less than 3%.

A "high-melting" 1% agarose gel in water (Standard Low-m$_r$ Agarose, Biorad) was cast on a 12.5 cm×20 cm GelBond support (FMC, Rockland, Me.) at a thickness of 1.5 mm. Holes approximately 4 mm in diameter were made in the gel at defined positions using a pipette tip connected to a vacuum line. Single $^{14}$C-test beads from each ratio were placed in the holes, and the holes sealed with warm agarose (~60° C.). The agarose gel was air-dried overnight, then stapled and exposed to autoradiography film (Hyperfilm-MP, Amersham, Arlington Heights, Ill.) in an 8"×10" stainless steel cassette (Fisher). Staple marks were later used to align the film with the gel. Films were developed using GBX Developer and GBX fixer (Sigma).

To determine the signal strengths of the spots observed on the film, the film was subjected to conventional image analysis (Image Pro, Media Cybernetics, Silver Spring, Md.). Signal strength is given as the signal intensity multiplied by the signal area. Twenty-five beads were next excised from the gel by scratching a square area around each bead with a scalpel, then applying 1–2 μl water to rehydrate the agarose instantaneously. Each bead was then scooped out with the scalpel and transferred to a scintillation vial containing 1 ml water. Agarose remaining on the beads was removed by heating the vials in a water bath at 95° C. for 15 minutes, followed by sonication at 80° C. for 10 minutes. The beads were counted for 60 minutes, giving a standard deviation of less than 2%, to determine the labeling required to generate each signal.

In an attempt to improve the sensitivity, additional gels containing radioactive beads were treated with fluorographic reagents. Gels soaked in Amplify (Amersham) or 1M sodium salicylate (22) for thirty minutes developed a dense layer of crystals upon drying. These crystals made bead identification difficult. Furthermore, they could likely scratch the autoradiography film, generating false images. Agarose gels containing 10% by volume of the above fluorographic reagents also crystallized upon drying. Therefore, the use of these fluorographic reagents is incompatible with the radiological approach described here.

Radiological Screening of Libraries

Library beads, 20 mg in dry weight per experiment, were first mixed with 1 ml of blocking solution to block non-specific interactions between the peptides and $^{14}$C-protein. For screenings against S-protein, 2% bovine serum albumin (BSA, Sigma) in PBS containing 0.05% Tween (Sigma) was used as blocking solution. For screenings against fibrinogen, either 2% BSA in PBS with 0.05% Tween or Blocker™Casein (1%) in PBS (Pierce) was used. Each mixture of beads and blocking solution was incubated in a Cryotube (Nunc, Denmark) for 2 hours on a tube rotator.

The blocked library beads were then exposed to target protein by pipetting the $^{14}$C-labeled protein directly into the mixture of beads and blocking solution. For S-protein experiments, 35 μl of the 30 μM $^{14}$C-S-protein solution was added, yielding a final S-protein concentration of 1 μM. For fibrinogen experiments, 13 μl and 65 μl of the 4 μM $^{14}$C-fibrinogen solution was added, yielding final fibrinogen concentrations of 50 nM and 250 nM, respectively. The mixtures of beads, blocking solution, and protein solution were further rotated for 1.5 hours (S-protein experiment) and for 1 hour (fibrinogen experiment).

After completion of blocking and binding, the beads were transferred to a Polyprep column (Biorad) and rinsed with PBS containing 0.05% Tween 20 (Sigma) until the column flow-through reached background DPM levels. The total rinsing volumes were 200 ml and 140 ml for S-protein and fibrinogen, respectively. For comparison, the approximate volume of 20 mg beads is only 60 μl.

A 1% high-melting agarose gel was cast on a GelBond support (20 cm×20 cm) at a thickness of 1.5 mm. Two large "windows" of 8 cm×12 cm, together with two small windows of 8 cm×4 cm, were cut out leaving a 2 cm "frame". This frame prevents the spreading of beads to the edges of the plate and serves as a practical "handle". Each window was separated by one cm of gel.

Rinsed beads were transferred in 2 ml PBS containing 0.05% Tween 20 to a 50 ml conical tube (Nunc). To the tube, 13 ml of a 1% solution of "low-melting" agarose gel (Low Melt Preparative Grade; Biorad) at 30° C. were added. At this temperature, the risk of denaturation and dissociation of protein is reduced. The suspension of agarose gel and beads was mixed by gentle swirling, then poured inside one of the large "windows" to a thickness of 1.5 mm and a density of 0.2 mg beads/cm$^2$agarose gel. This bead density gives an even monolayer and facilitates identification and isolation of individual beads. To minimize any loss of beads, the tube was rinsed a second time with 5 ml agarose gel. This gel was poured out into one of the small windows. Beads from another screening experiment were plated out into the remaining two windows in a similar fashion.

The agarose gel was air dried overnight and exposed to autoradiography film. For S-protein experiments, the exposure time was 1 day, followed by a repeated exposure for 3 days. For fibrinogen experiments, the exposure time was 2 days, followed by a repeated exposure for 25 days. Positive beads were identified by careful alignment of the developed film and agarose gel (via staple holes), and isolated as described previously.

Beads to be sequenced were transferred to a microcentrifuge tube containing water. Agarose remaining on the beads was removed by heating the tubes for 5 minutes in a 70° C. water bath followed by sonication for 5 minutes in warm water. The water in the tubes was carefully aspirated and fresh water added. This procedure was repeated until no agarose was seen when examining the bead under a microscope. Each bead was then sequenced by Edman degradation.

For beads to be counted in scintillation counter, the isolated beads were transferred directly to 1 ml water in a scintillation vial, which was heated at 70° C. for 10 minutes followed by sonication in warm water for 10 minutes. The beads were counted for 2 h, yielding a standard deviation of less than 2%.

Affinity Purification of Fibrinogen

Dried peptide resins were packed into 0.6 ml columns (0.4 cm×5 cm, Thomson, Va.), and evaluated on a Waters HPLCsystem (Milford, Mass.) with a UV-detector (Knauer, Germany) monitoring at 280 nm. The columns were conditioned with over 5 volumes of 20% ethanol in water, followed by a minimum of 5 volumes of water.

Human fibrinogen was purchased from Enzymes Research Labs (South Bend, Ind.), and 25% human serum albumin (HSA) was a donation from the Bayer Corporation (Clayton, N.C.). The following buffers were used for both dissolving fibrinogen and diluting HSA.

| Buffer A | PBS with Tween (Sigma): 10 mM sodium phosphate, 0.14 M NaCl, 3 mM KCl and 0.05% Tween 20, pH 7.4 |
|---|---|
| Buffer B | 100 mM e-amino-caproic acid (Sigma), 50 mM sodium citrate (Fisher), 150 mM NaCl (Sigma), adjusted with HCl (Fisher) to pH 7.1. |

Because a clotted precipitate was observed in mixtures of fibrinogen and HSA, these samples were centrifuged before injection.

(a) Preliminary Test for Fibrinogen Binding to Peptide Resin Columns:

Peptide resin columns were equilibrated in Buffer A. The following program was used for each column run: From time 0–15 minutes, Buffer A was applied. At time 10 minutes, a 50 μl sample was injected onto the column with a 50 μl sample loop. From time 15–20 minutes, bound protein was step-eluted by switching to 0.4M acetic acid (Fisher), pH 2.6. The column was then re-equilibrated with Buffer A from time 20–30 minutes. A flow rate of 1 ml/min was used. For each column two injections were made: #1 Buffer A (blank); #2 10 μg/μl Fibrinogen dissolved in Buffer A.

(b) Purification on the WQETYQ-column (SEQ ID NO 2):

This column was equilibrated in Buffer A, and the following program was used for each column run: From time 0–15 minutes, Buffer A was applied. At time 5 minutes, a 50 μl sample dissolved in buffer A was injected onto the column with a 100 μl sample loop. From time 15–20 minutes, bound protein was step-eluted by switching to 0.1M acetic acid, pH 2.9, followed by 0.4M acetic acid, pH 2.6, from time 20–21 minutes. The column was then re-equilibrated with Buffer A from time 21–30 minutes. During the column run, the flow rate was 1 ml/min from time 0–21 minutes; it was increased to 2 ml/min from time 21–30 minutes.

In total, seven injections were made: #1 Buffer A (blank); #2 100 μg/μl HSA; #3 20 μg/μl Fibrinogen; #4 Mixture of 5 μg/μl Fibrinogen and 90 μg/μl HSA; #5 Mixture of 10 μg/μl Fibrinogen and 75 μg/μl HSA; #6 Mixture of 20 μg/μl Fibrinogen and 50 μg/μl HSA; #7 20 μg/μl Fibrinogen.

(c) Purification on the WQEHYN- and the YENYGY-columns (SEQ ID NOS 1 and 3, respectively):

After equilibrating in Buffer B, the following program was used for each column run: From time 0–15 minutes, Buffer B was applied. At time 5 minutes, 50 μL sample dissolved in Buffer B was injected onto the column with a 100 μl sample loop. From time 15–20 minutes, bound protein was step-eluted by switching to 20 mM acetic acid, pH 3.2, followed by 0.4M acetic acid, pH 2.6, from time 20–23 minutes. The column was then re-equilibrated with Buffer B from time 23–30 minutes. During the column run, the flow rate was 1 ml/min from time 0–23 minutes, then it was increased to 2 ml/min from time 23–30 minutes. In total, for each column seven injections were made: #1 Buffer B (blank); #2 for WQEHYN-column: 50 μg/μl HSA, and for YENYGY-column: 100 μg/μl HSA; #3 20 μg/μl Fibrinogen; #4 Mixture of 5 μg/μl Fibrinogen and 50 μg/μl HSA; #5 Mixture of 10 μg/μl Fibrinogen and 50 μg/μl HSA; #6 Mixture of 20 μg/μl Fibrinogen and 50 μg/μl HSA; #7 20 μg/μl Fibrinogen.

In parts (b) and (c), eluted protein was collected in 1.25 ml fractions, some in which pH was measured. The fractions were not re-adjusted to a neutral pH. The purity of the eluted protein was assessed by SDS-PAGE (Biorad) of non-reduced as well as of reduced samples. Broad Range Standards (Biorad) were used as molecular weight standards, and dithiothreitol (Sigma) was used as the reducing agent. Eluted protein was centrifuged and supernatant collected for determination of fibrinogen concentration by $A_{280}$.

Results

Sensitivity

To estimate the sensitivity and resolution of the $^{14}$C-radiological approach, aminated resin beads were methylated with $^{14}$C-formaldehyde at varying concentrations. The degree of methylation correlated with the amount of $^{14}$C-formaldehyde employed, and bead counts ranged from 70–8000 DPM/bead. The experiment with lower concentrations of $^{14}$C-formaldehyde to examine the system sensitivity below 70 DPM/bead was not repeated.

Figure 1:
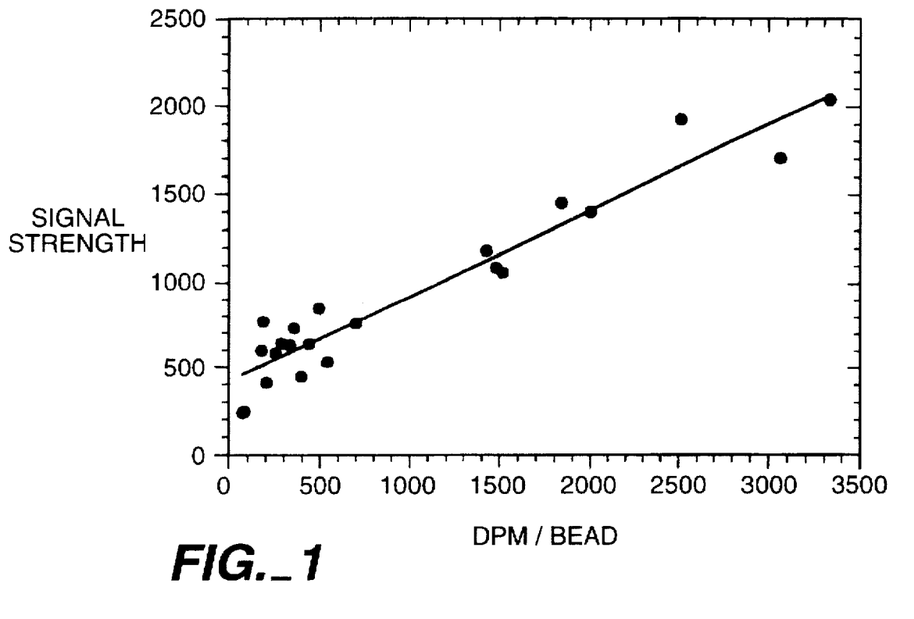
FIG. 1 shows signal strength as a function of DPM/Bead. Test beads which generated images on autoradiography film were isolated and counted (values are corrected for background). The signal strength, given as signal intensity multiplied by signal area, was determined using conventional image analysis.

Some of the $^{14}$C-test beads were immoblized in an agarose gel and exposed to autoradiography film for 25 hours. Each test bead generated a distinct image on the film. Test beads were isolated from the gel and counted to correlate signal strength, as determined by conventional image analysis, with DPM of the corresponding bead. The correlation, shown in FIG. 1, is linear (R=0.96). Since there were no data points below 70 DPM/bead, the line can not be extrapolated to zero signal strength at zero labeling.

A sensitivity on the order of 70 DPM/bead is appropriate for screening peptide libraries. Due to the limited amount of protein that can bind to a single bead and the low labeling yields often desired or achieved on the protein itself, low levels of bound protein must be detected. Results from screening against $^{14}$C-S-protein (described in the next section) show that beads with as little as 40 DPM can be detected after a 3-day exposure.

Proof of Principle

Ribonuclease S-protein binds YNFEVL-peptide (SEQ ID NO 4) (3,17). Therefore, spiking one of two portions of a solid phase peptide library with YNFEVL-beads, followed by screening both portions against $^{14}$C-labeled S-protein, serves as a "proof of principle" experiment; that is, positive film signals corresponding to the YNFEVL-beads would validate the $^{14}$C-radiological methodology.

S-protein was $^{14}$C-labeled with a yield of $8.4 \times 10^{14}$ DPM/mol, corresponding to 38% of the maximal labeling yield. The YNFEVL (SEQ ID NO 4) peptide was synthesized at a density of 120 μmol/g resin, and beads were randomly picked with respect to size. The peptide library was divided into two aliquots, each containing approximately 40,000 beads. One aliquot was spiked with 200 YNFEVL-beads. Both aliquots were screened against $^{14}$C-S-protein at a protein concentration of 1 mM in PBS with 0.05% Tween 20 containing 2% BSA. The beads were then plated out in agarose and exposed to autoradiography film.

From the spiked bead mixture, 170 beads generated images after a one day exposure; 180 beads after a three day exposure. Less than five beads produced faint, disperse signals in the mixture without YNFEVL beads (SEQ ID NO 4).

Furthermore, 55 positive beads, i.e. beads that generated images on autoradiography film, were isolated together with 11 negative beads from the agarose gel. Of the 55 positive beads, 8 beads were randomly selected to be sequenced. Sequencing of these 8 beads all resulted in the YNFEVL sequence (SEQ ID NO 4).

The yield of the first amino acid residue, Y, of these sequenced beads ranged from 36–149 pmol/bead, with an average of 70 pmol/bead. This value is only an estimate, since the yield of the first residue does not equal the true amount of peptide on a single bead.

To determine the amount of protein bound to a particular bead, the remaining isolated beads were counted in a scintillation counter. After subtracting the background (33 DPM), values ranged from 41–243 DPM/bead corresponding to 49–289 fmol protein/bead, with an average of 133 fmol protein/bead. Thus the peptide to protein ratio approximates 500 YNFEVL-peptide molecules (SEQ ID NO 4) to 1 S-protein molecule.

Figure 2:
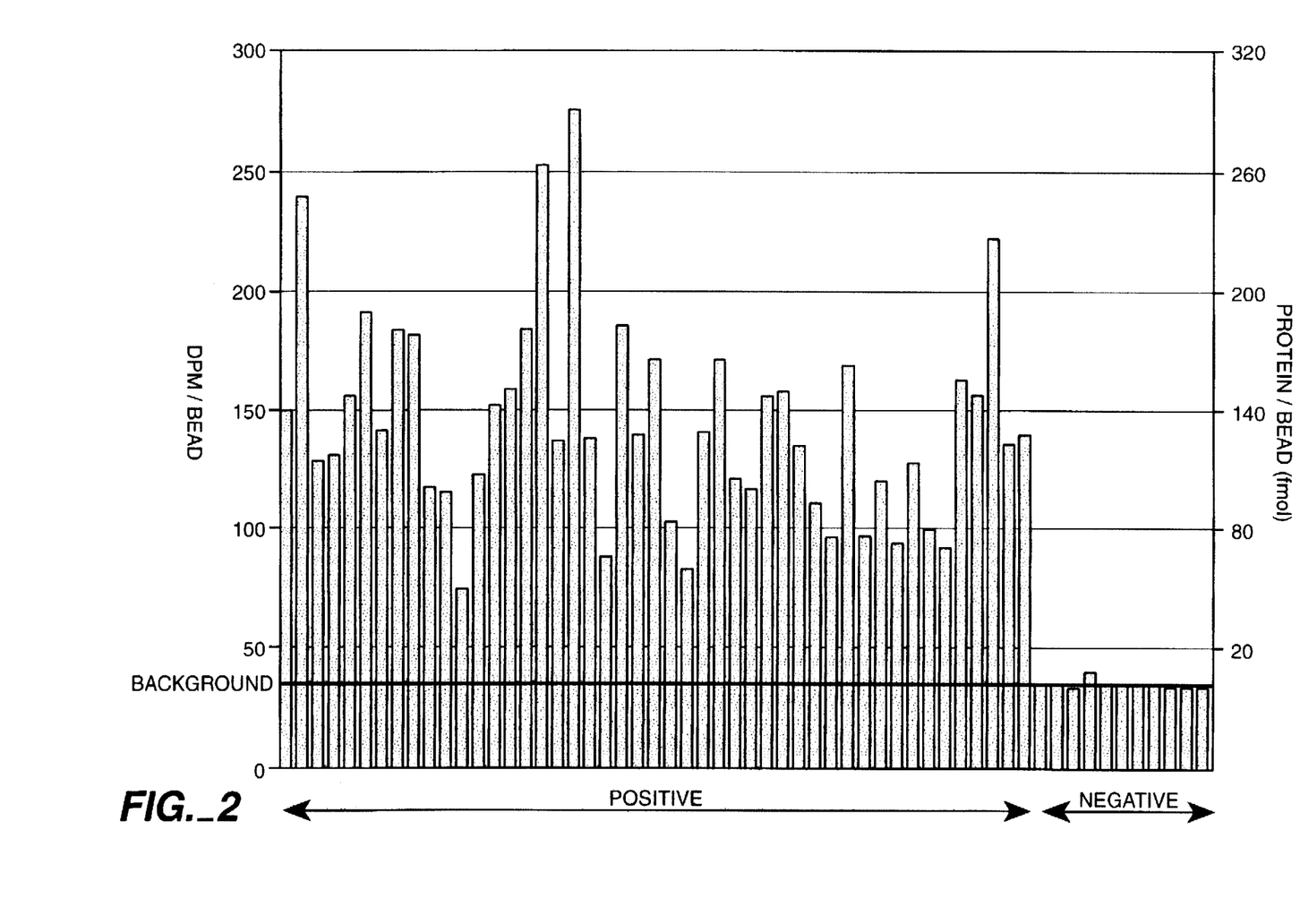
FIG. 2 shows variation in DPM and the amount of protein bound to single beads isolated from the screening of peptide library beads spiked with YNFEVL-beads (SEQ ID NO 4) against $^{14}$C-S-protein. The DPM values shown are not corrected for background. The corresponding amount of protein bound to a single bead is corrected for background.

FIG. 2 shows the variation in DPM/bead and the resulting variation in the amount of protein bound on beads isolated from the agarose gel. The 11 negative beads, also counted, were at the background level of the scintillation counter.

Screening against Fibrinogen

Aliquots of the hexapeptide library (approximately 40,000 beads per aliquot) were screened against $^{14}$C-labeled fibrinogen to find ligands for the affinity purification of fibrinogen. Fibrinogen was labeled with $^{14}$C at a yield of $1.3 \times 10^{15}$ DPM/mole, representing 2.5% of the maximal possible labeling yield. Four different screening experiments were set up and run in parallel, testing two different blocking systems, 2% BSA in PBS with Tween and 1% casein in PBS, and two different concentrations of fibrinogen, 50 nM and 250 nM. The library beads were plated out as described previously and exposed to autoradiography film for 2 days. The number of positive signals generated on the film are given in Table 1.

TABLE 1

Effect of Protein Concentration and Blocking Conditions on the Number of Positive Signals Generated on Autoradiography Film

| $^{14}$C-Fibrinogen Concentration | Blocking Conditions | Positive Signals on Film |
|---|---|---|
| 50 nM | 2% BSA in PBS + Tween | 2–5% |
| 250 nM | 2% BSA in PBS + Tween | 10–20% |
| 50 nM | 1% Casein in PBS | 0 |
| 250 nM | 1% Casein in PBS | 5 |

For both fibrinogen concentrations tested, 2% BSA was unable to block non-specific interactions: up to 20% of the total number of beads screened generated images. When blocking with a 1% casein solution, however, the background level on the autoradiography film was close to zero. No beads generated images on autoradiography film using a fibrinogen concentration of 50 nM. Only 5 beads generated images using the higher concentration, 250 nM. To verify these results, the casein-blocked gel was re-exposed to a new film for 25 days. The five signals were significantly stronger than background images, which started to appear after this extraordinarily long exposure time. These five beads were isolated and sequenced (see Table 2).

TABLE 2

Peptide Sequences Obtained by Screening Against $^{14}$C-Fibrinogen

| Bead Peptide Sequence | SEQ ID NO | Yield of 1st Residue | Repetitive Yield |
|---|---|---|---|
| No. 1 W-Q-E-H-Y-N | 1 | 66 pmoles | 79% |
| No. 2 W-Q-E-T-Y-Q | 2 | 385 pmoles | 82% |
| No. 3 P-W-X-X-X-X | — | 309 pmoles | — |
| No. 4 Y-E-N-Y-G-Y | 3 | 917 pmoles | 75% |
| No. 5 W-E-Q-(S)-N-P | 5 | 72 pmoles | 66% |

The truncated sequence of bead no. 3, PWX, could be due to either incomplete peptide synthesis or to trace amounts of peptidases present in the fibrinogen preparation used. It was difficult to interpret the fourth residue of bead 5, but a serine seemed most likely.

EXAMPLE

Affinity Purification of Fibrinogen

Four of the peptides (all but No. 3) listed in Table 2 were re-synthesized directly onto resin. The obtained peptide densities were in the range of 0.1–0.2 mmol/g (WQEHYN: 0.10 mmol/g; WQETYQ: 0.15 mmol/g; YENYGY: 0.17 mmol/g; WEQSNP 0.16 mmol/g)

Figure 3:
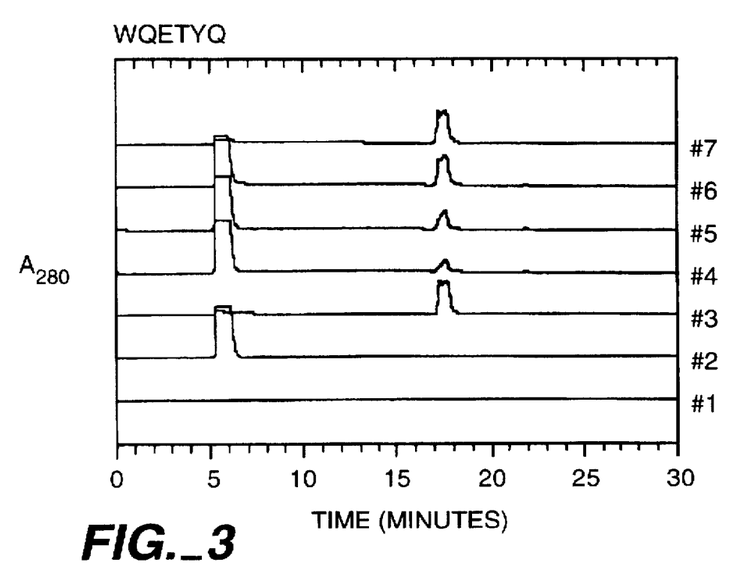
FIG. 3 shows chromatograms of the purification of fibrinogen from a mixture with human serum albumin on the WQETYQ-column (SEQ ID NO 2). Samples of 50 µl were injected at time 5 minutes. #1 Buffer A (blank); #2 100 µg/µl HSA; #3 20 µg/µl Fibrinogen; #4 Mixture of 5 µg/µl Fibrinogen and 90 µg/µl HSA; #5 Mixture of 10 µg/µl Fibrinogen and 75 µg/µl HSA; #6 Mixture of 20 µg/µl Fibrinogen and 50 µg/µl HSA; #7 20 µg/µl Fibrinogen.
Figure 4:
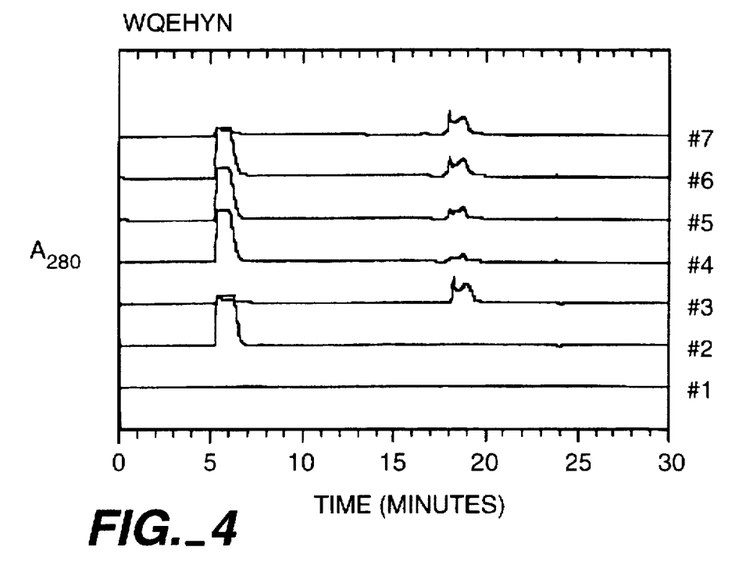
FIG. 4 shows chromatograms of the purification of fibrinogen from a mixture with human serum albumin on the WQEHYN-column (SEQ ID NO 1). Samples of 50 μl were injected at time 5 minutes. #1 Buffer B (blank); #2 50 μg/μl HSA; #3 20 μg/μl Fibrinogen; #4 Mixture of 5 μg/μl Fibrinogen and 50 μg/μl HSA; #5 Mixture of 10 μg/μl Fibrinogen and 50 μg/μl HSA; #6 Mixture of 20 μg/μl Fibrinogen and 50 μg/μl HSA; #7 20 μg/μl Fibrinogen.
Figure 5:
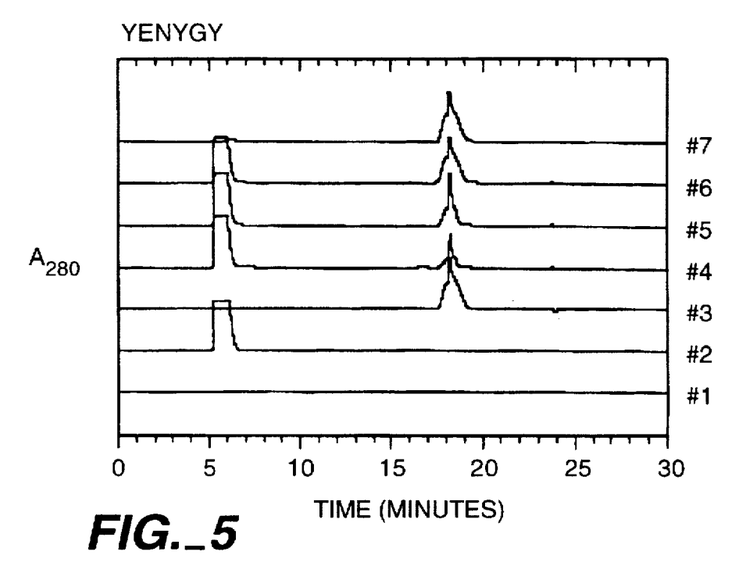
FIG. 5 shows chromatograms of the purification of fibrinogen from a mixture with human serum albumin on the YENYGY-column (SEQ ID NO 3). Samples of 50 μl were injected at time 5 minutes. #1 Buffer B (blank); #2 100 μg/μl HSA; #3 20 μg/μl Fibrinogen; #4 Mixture of 5 μg/μl Fibrinogen and 50 μg/μl HSA; #5 Mixture of 10 μg/μl Fibrinogen and 50 μg/μl HSA; #6 Mixture of 20 μg/μl Fibrinogen and 50 μg/μl HSA, #7 20 μg/μl Fibrinogen.

Three of the peptides, WQEHYN, WQETYQ, and YENYGY bound fibrinogen (SEQ ID NOS 1, 2, and 3, respectively), and none of these peptides bound HSA under the conditions described in the experimental section (see FIGS. 3–5). The peptide WEQSNP (SEQ ID NO 5) did not bind fibrinogen in the preliminary test nor in Buffer B (results not shown).

Furthermore, all three fibrinogen-binding peptides captured fibrinogen selectively from a mixture with HSA. The presence of HSA in the injection mixture did not alter the elution profile of fibrinogen (see FIGS. 3–5).

For these binding studies Buffer A, which is identical to the buffer used in the screening of the peptide library, was initially used. However, Buffer B was later used because it is more suitable for fibrinogen purification since it contains citrate and EACA, both with anti-coagulatory effects. Later tests showed that all three peptides bound fibrinogen in both Buffer A and Buffer B (results not shown).

Fibrinogen was eluted from the WQETYQ-column using 0.1M acetic acid and from the WQEHYN- and YENYGY-columns using 20 mM acetic acid. No additional protein was eluted from the columns by switching to 0.4M acetic acid. When measuring pH in the eluted fractions, values of pH 5-6 were obtained. This indicates that a complete breakthrough of the acetic acid, pH 3, was not required for the elution of fibrinogen. Eluting fibrinogen with even low concentrations of acetic acid may result in loss of biological activity. However, this was not an important issue for these experiments. Instead, the objective here was to elute as much protein as possible.

The purification of fibrinogen from a mixture with HSA was assessed by SDS-PAGE of non-reduced as well as reduced samples. In its non-reduced form, fibrinogen, which has a molecular weight of 340,000 (23) was seen at the top of the gel. In its reduced form, bands were seen with approximately Mr=66,000 (Aα-chains), Mr=55,000 (Bβ-chains), Mr=49,000 (γ-chains), and Mr>200,000. The fibrinogen supplied by the manufacturer was depleted of plasminogen and vWF, but not of fibronectin, which contains subunits of Mr>200,000 (23). Hence, the high molecular weight band may be due to fibronectin.

For the three columns, the amount of fibrinogen eluted correlated with the amount injected (Table 3). In sample mixtures with HSA, a clotted precipitate formed. As a result, the actual amount of fibrinogen injected may have been less than that listed above. Nevertheless, up to 50% of the "theoretical" amount of injected fibrinogen was recovered. Protein precipitation or denaturation may account for further loss of fibrinogen in the column.

TABLE 3

Fibrinogen Recovery from Peptide Columns

| Column Run | Injected Amount of Fibrinogen (µg) | WQEHYN-Column Peak (µg) (SEQ ID NO 1) | WQETYQ-Column Peak (µg) (SEQ ID NO 2) | YENYGY-Column Peak (µg) (SEQ ID NO 3) |
|---|---|---|---|---|
| #3 | 1000 | 330 | 360 | 530 |
| #4 | 250 | 70 | 100 | 150 |
| #5 | 500 | 140 | 150 | 280 |
| #6 | 1000 | 220 | 310 | 520 |
| #7 | 1000 | 240 | 340 | 530 |

Discussion

The objective of this work was to develop a method for detecting protein specifically bound to single combinatorial peptide library beads using $^{14}C$ as a radioactive label. A further objective was to identify peptides that would serve as affinity ligands for fibrinogen purification. $^{14}C$ was chosen as a radioactive label because it is a weak beta-emitter, with a migration distance of only 24 cm in air and 0.3 mm in water (24, 25). Hence, compared to other isotopes, e.g. $^{125}I$, human exposure to radioactive emission is reduced.

A crucial question was whether a $^{14}C$-based signal coming from one bead would be strong enough to be detected by autoradiography. In addition, it was important to be able to distinguish signals and align them to single beads. Accordingly, the first determination made was the required amount of radioactivity on a bead, as well as the exposure time necessary, to generate a detectable signal on autoradiography film. The experiment using $^{14}C$-Test Beads shows that it is possible to obtain clear and distinct signals from beads labeled with as little as 70 DPM/bead after a 25 hour exposure time at room temperature. Neither amplifying screens and reagents nor low temperature exposures are needed.

As illustrated by the YNFEVL/S-Protein experiment, this method can be applied to peptide/protein interactions of even moderate affinity. The association constant for binding S-protein to the YNFEVL-peptide is no larger than $10^4$–$10^5$ $M^{-1}$ (3). A very high fraction of the added YNFEVL-beads generated signals on the film after a one day exposure, and the non-spiked library showed a very low background level. For this particular system, 2% BSA effectively blocked non-specific interactions.

The radiological approach allows one to test several variables simultaneously and compare the results directly. For example, the effect of the fibrinogen concentration was studied together with the effect of the blocking system on the number of positives identified. Since exposing a gel to autoradiography film is non-destructive, exposure can easily be repeated in the case of a too weak, or an otherwise non-satisfactory image on a film.

The exposure time (from a day up to a week) usually needed to obtain a distinct image on the film may be considered a disadvantage of this method. On the other hand, the fact that it is a direct detection system increases the chances of finding true, specific binders.

Another disadvantage of the $^{14}C$ radiological approach is the potential modification of the target due to the methylation process. A labeling yield on the order of $10^{14}$–$10^{15}$ DPM/mole, corresponding to 1–10 moles of $^{14}C$-methyl groups per mole of protein, is still suitable for obtaining images on autoradiography film. Nevertheless, one must verify that the peptides bind the non-modified target under relevant binding conditions.

Three peptides were identified that bind and purify fibrinogen from mixtures with HSA. These peptides consist of both hydrophilic and hydrophobic residues, and they all contain the negatively charged glutamic acid as well as either tryptophan and/or tyrosine. The statistical probability of finding two peptides with exactly four out of six residues matching at the same locations, as was the case for the peptides WQEHYN and WQETYQ, is significantly low (p=0.000127, see Appendix 1). This illustrates the selectivity of the screening method. Although the probability of this event happening is low, it is reasonable considering the number of beads screened. For example, the 20 mg of library (corresponding to 40,000 beads) used in this experiment should contain approximately five sequences with four out of six matches.

The sequences obtained were from only a small fraction of the library. These leads can serve as templates for further optimization e.g. by point mutation or further screening of a more restricted library.

Conclusion

A radiological screening approach offers high sensitivity and resolution with a simple and direct methodology. Even femtomolar amounts of protein bound to a single bead can be detected. Screening against $^{14}C$-fibrinogen resulted in three peptide sequences that bound and purified fibrinogen from mixtures with HSA. Two of these peptides displayed a high degree of homology. Hence, peptides obtained using this screening technique make suitable affinity ligands for column chromatography.

The above examples are intended to illustrate the invention and it is thought variations will occur to those skilled in the art. Accordingly, it is intended that the scope of the invention should be limited only by the claims below.

References

1. Baumbach, G. A. and Hammond, D. J. (1992), Protein Purification Using Affinity Ligands from Peptide Libraries, BioPharm, May, 24–35.
2. Buettner, J. A., Dadd, C. A., Baumbach, G. A., Masecar, B. L., Hammond, D. J. (1996), Chemically derived peptide libaries: A new resin and methodology for lead identification, Int.J.Peptide Protein Res., 47, 70–83.
3. Huang, P. Y. and Carbonell, R. G. (1995), Affinity Purification of Proteins Using Ligands Derived from Peptide Libraries, Biotechnology and Bioengineering, 47, 288–297.
4. Huang, P. Y., Baumbach, G. A., Dadd, C. A., Buettner, J. A., Masecar, B. L., Hentsch, M., Hammond, D. J., Carbonell, R. G. (1996), Affinity Purification of von Willebrand Factor Using Ligands Derived from Peptide Libraries, Bioorganic & Medicinal Chemistry, 4, 699–708.

5. Furka, A., Sebestyen, F., Asgedom, M., Dibo, G. (1992). General method for rapid synthesis of multicomponent peptide mixtures. Int. J. Peptide Protein Res., 37, 487–493.
6. Lam, K. S., Salmon, S. E., Hersh, E. M., Hruby, V. J., Kazmierski, W. M., Knapp, R. J. (1991). A new type of synthetic peptide library for identifying ligand-binding activity. Nature, 354, 82–84.
7. Houghten, R. A., Pinilla, C., Blondelle, S. E., Appel, J. R., Dooley, C. T., Cuervo, J. H. (1991). Generation and use of synthetic peptide combinatorial libraries for basic research and drug discovery. Nature, 354, 84–86.
8. Lam, K. S., Wade, S., Abdul-Latif, F., Lebl, M. (1995). Application of a dual color detection scheme in the screening of a random combinatorial peptide library. Journal of Immunological Methods, 180, 219–223
9. Meldal, M., Svendsen, I., Breddam, K., Auzanneau, F.-I. (1994). Portion-mixing peptide libraries of quenched fluorogenic substrates for complete subsite mapping of endoprotease specificity.Proc. Natl. Acad. Sci. USA 91, 3314–3318
10. Meldal, M. and Svendsen, I. (1995). Direct visualization of enzyme inhibitors using a portion mixing inhibitor library containing a quenched fluorogenic peptide substrate. Part 1. Inhibitors for subtilisin Carlsberg, J. Chem. Soc. Perkin Trans. 1591–1596
11. Needels, M. C., Jones, D. G., Tate, E. H., Heinkel, G. L., Kochersperger, L. M., Dower, W. J., Barrett, R. W., Gallop, M. A. (1993). Generation and screening of an oligonucleotide-encoded synthetic peptide library. Proc. Natl. Acad. Sci. USA 90, 10700–10704
12. Lebl, M., Krchnak, V., Sepetov, N. F., Seligmann, B., Strop, P., Felder, S. (1995). One-Bead-One-Structure Combinatorial Libraries. Biopolymers, 37, 177–198.
13. Kassarjian, A., Schellenberger, V., Turck, C. W. (1993). Screening of Synthetic Peptide Libraries with Radiolabeled Acceptor Molecules. Peptide Research, 6, 129–133.
14. Turck, C. W. (1994). Radioactive Screening of Synthetic Peptide Libraries. Methods: A Companion to Methods in Enzymology, 6, 396–400.
15. Wu, J., Ma, Q. N., Lam, K. S. (1994). Identifying Substrate Motifs of Protein Kinases by a Random Library Approach. Biochemistry, 33, 14825–14833.
16. Lam, K. S., Wu, J., Lou, Q. (1995). Identification and characterization of a novel synthetic peptide substrate specific for Src-family protein tyrosine kinases, Int.J.Peptide Protein Res., 45, 587–592.
17. Smith, G. P., Schultz, D. A., Ladbury, J. E. (1993). A ribonuclease S-peptide antagonist discovered with a bacteriophage display library. Gene, 128, 37–42.
18. Brennan, M. (1991). Fibrin Glue. Blood Reviews, 5, 240–244.
19. Godel, H., Seitz, P., Verhoef, M. (1992). Automated Amino Acid Analysis Using Combined OPA and FMOC-Cl Precolumn Derivatization. LC-GC International, 5, 44–49.
20. Miller, C. G. (1994). Adsorptive Biphasic Column Technology for Protein Sequence Analysis and Protein Chemical Modification. Methods: A Companion to Methods in Enzymology, 6, 315–333.
21. Jentoft, N. and Dearborn, D.G. (1983). Protein Labeling by Reductive Alkylation. Methods in Enzymology, 91, 570–579.
22. Chamberlain, J. P. (1979). Fluorographic Detection of Radioactivity in Polyacrylamide Gels with the Water-Soluble Fluor, Sodium Salicylate, Analytical Biochemistry, 98, 132–135.
23. Haeberli, A. (1992). Human Protein Data, VCH Publishers, New York
24. Amersham (1996), Lifescience Catalog, 190.
25. Cember, H. (1996). Introduction to Health Physics, 119–131, McGraw-Hill, N.Y.
26. Chistyakov, V. P., Sevast'yanov, B. A., Zakharov, V. K. (1987). Probability Theory for Engineers, 8–11, Optimization Software, Inc., N.Y.
27. Buettner, J. A., Dadd, C. A., Baumbach, G. A., and Hammond, D. J., Fibrinogen Binding Peptides, U.S. Patent application Ser. No. 08/595,718.

APPENDIX 1

In determining the probability of having two sequences with four out of six matches in a 6X library, the following assumptions are made:

All possible peptides are present and in equal amounts in the library

An aliquot of the library is taken out completely randomly Here, a match is defined as an equal value at the same position.

The two six-amino-acid sequences are considered as one sequence consisting of twelve positions. Because the library was made with 18 different amino acids, the number of combinations of the first six positions of the sequence is $18^6$. The number of combinations of the next four out of six amino acids, matching four out of the six positions just defined, is given as "six choose four", or $$\frac{6!}{(4!(6-4)!)}$$

Because the remaining two positions of the sequence do not match the positions in the first string of six, the number of combinations of the other two amino acids is $17^2$ combinations.

With the total number of combinations of the twelve-amino-acid sequence as $18^{12}$, the probability (26) is calculated to be $$\text{PROBABILITY} = \frac{(18^6)\left(\frac{6!}{4!(6-4)!}\right)(17)(17)}{18^{12}} = 0.000127$$

---

What is claimed is:

1. A composition comprising a peptide having an available fibrinogen binding domain, wherein the binding domain is selected from the group consisting of Trp-Gln-Glu-His-Tyr-Asn(SEQ ID NO=1), Trp-Gln-Glu-Thr-Tyr-Gln(SEQ ID NO=2), and Tyr-Glu-Asn-Tyr-Gly-Tyr(SEQ ID NO=3).

2. The composition of claim 1, further comprising fibrinogen bound to the binding domain.